(12) United States Patent
Ballam et al.

(10) Patent No.: US 10,085,639 B2
(45) Date of Patent: Oct. 2, 2018

(54) TRACKING CONTACT QUALITY TO VITAL SIGNS MEASUREMENT SENSORS

(71) Applicant: QUALCOMM Incorporated, San Diego, CA (US)

(72) Inventors: Robert Scott Ballam, Eatons Hill (AU); Robert Bruce Ganton, San Diego, CA (US); Stephen Dickey, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 15/079,280

(22) Filed: Mar. 24, 2016

(65) Prior Publication Data

US 2017/0273560 A1 Sep. 28, 2017

(51) Int. Cl.
*A61B 5/00* (2006.01)

(52) U.S. Cl.
CPC ................... *A61B 5/0002* (2013.01)

(58) Field of Classification Search
CPC ..... A61B 5/0002; A61B 5/053; A61B 5/6885; A61B 5/7203; A61B 5/6843; G01R 1/06; G01R 1/18
See application file for complete search history.

(56) References Cited

U.S. PATENT DOCUMENTS 3,685,454 A 8/1972 Ogilvy et al.
6,740,042 B1* 5/2004 Lerner ..................... A61B 8/04
600/453
7,471,969 B2 12/2008 Diab et al.
8,483,977 B1* 7/2013 Johnnie ............. G01N 29/0609
702/36

(Continued)

FOREIGN PATENT DOCUMENTS

JP 2004135854 A 5/2004
WO 2009147615 A1 12/2009

(Continued)

OTHER PUBLICATIONS

Teja B.R., "Calculation of Blood Pulse Transit Time from PPG," Department of Biotechnology and Medical Engineering, National Institute of Technology, Rourkela, 2012, 54 Pages.

(Continued)

*Primary Examiner* — Orlando Bousono
(74) *Attorney, Agent, or Firm* — Kilpatrick Townsend & Stockton

(57) ABSTRACT

Various embodiments include a variety of sensors, such as a pulse oximeter, configured to track a dynamic component of a sensor and take an action based on a characteristic of the dynamic component. Some embodiments may include determining a gain applied to a signal of the sensor, determining whether the gain is discontinuous, and indicating that a sensor measurement associated with the signal is low quality in response to determining that the gain applied is discontinuous. Some embodiments may include determining a peak-to-peak voltage of an output of a sensor, determining whether the peak-to-peak voltage is within an acceptable peak-to-peak voltage range, and indicating that a measurement associated with the received signal is low quality in response to determining that the peak-to-peak voltage is outside the acceptable peak-to-peak voltage range.

25 Claims, 7 Drawing Sheets

(56) References Cited

U.S. PATENT DOCUMENTS

| | | |
|---|---|---|
| 8,560,036 B2 | 10/2013 | Baker, Jr. |
| 8,998,815 B2 | 4/2015 | Venkatraman et al. |
| 2001/0010460 A1* | 8/2001 | Miller .................. G01V 3/088 324/67 |
| 2006/0122473 A1 | 6/2006 | Kill et al. |
| 2007/0167879 A1 | 7/2007 | Cochran |
| 2008/0027338 A1 | 1/2008 | Lu et al. |
| 2008/0273768 A1* | 11/2008 | Dennis .................. G06K 9/0012 382/124 |
| 2009/0112080 A1* | 4/2009 | Matthews ............ A61B 5/0428 600/393 |
| 2009/0259137 A1* | 10/2009 | Delic .................... A61B 5/6843 600/545 |
| 2010/0013952 A1* | 1/2010 | Kwon .................... H04N 9/735 348/223.1 |
| 2011/0025348 A1* | 2/2011 | Chetham ................ A61B 5/053 324/649 |
| 2013/0116576 A1* | 5/2013 | Morren ............... A61B 5/02014 600/479 |
| 2013/0211259 A1* | 8/2013 | Komistek ........... G06F 19/3443 600/440 |
| 2013/0296666 A1 | 11/2013 | Kumar et al. |
| 2014/0066795 A1 | 3/2014 | Ferdosi et al. |
| 2014/0088394 A1 | 3/2014 | Sunderland |
| 2014/0275872 A1 | 9/2014 | Merritt et al. |
| 2015/0002177 A1* | 1/2015 | Chetham ................ A61B 5/053 324/692 |

FOREIGN PATENT DOCUMENTS

| | | |
|---|---|---|
| WO | 2011007294 A1 | 1/2011 |
| WO | 2016040647 A2 | 3/2016 |

OTHER PUBLICATIONS

Partial International Search Report—PCT/US2017/019719—ISA/EPO—May 10, 2017.

International Search Report and Written Opinion—PCT/US2017/019719—ISA/EPO—Aug. 28, 2017.

\* cited by examiner

TRACKING CONTACT QUALITY TO VITAL SIGNS MEASUREMENT SENSORS

BACKGROUND

Continuous monitoring of vital signs with the ability to remotely monitor patient status is a growing field and the ability to incorporate multiple measurement capabilities into a single small unobtrusive patch that can be worn by a patient (i.e., a body worn patch) for multiple days at a time is a desirable feature. One such vital sign measurement is a blood oxygen level reading, often carried out by a pulse oximeter.

Pulse oximeters typically shine light of two different wavelengths through a body part of a patient and measure relative differences in amplitude of the original light and the received light at the two different wavelengths. For example, one wavelength may be red light generated by a red light emitting diode (LED) and the other wavelength may be infrared light generated by an infrared LED. The relative differences in amplitude of the original red light and original infrared light and the received red light and infrared light may be measured by a phototransistor. Blood with lower levels of oxygen may tend to absorb less infrared light and more red light. Alternatively, blood with higher levels of oxygen may tend to absorb more infrared light and less red light. Thus, a properly calibrated pulse oximeter can determine blood oxygen levels by emitting light of red and infrared wavelengths and measuring the relative amounts of red and infrared light after the light passes through a body part of a patient, such as a fingertip or earlobe. Additionally, the heart rate for the patient can be determined by the pulse oximeter based on the measurement of the received light. The movement of the patient and/or improper placement of the pulse oximeter can result in degradation of the blood oxygen level measurements and heart rate measurements by a pulse oximeter.

The waveform of measured light received by the pulse oximeter, also referred to as the received signal, has a high direct current (DC) (i.e., relatively static) component and a comparatively lower alternating current (AC) (i.e., dynamic) component resulting from changes in blood flow, the most important cause of such changes being the patient's pulse. Both the AC and DC level of the received signal may vary greatly depending on the color of the patient's skin and/or the quality of the contact between the sensor elements of the pulse oximeter and the patient's skin. As examples, the quality of the contact between the sensor elements of the pulse oximeter and the patient's skin may be impacted by the positioning of the sensor elements, the state of the patient's skin (e.g., oily, dry, etc.), the user's hair, etc.

To help mitigate the impact of the varying AC and DC level of the received signal, a pulse oximeter may include an automatic gain control (AGC) loop in the control algorithm for the sensor elements. The AGC loop may amplify or reduce the voltage amplitude of the received signal to a level suitable for use by the measurement circuitry of the pulse oximeter, such as to within threshold input levels of an analog-to-digital converter (A/D converter).

In a similar manner, the waveform of the light transmitted by the pulse oximeter, also referred to herein as the transmitted signal, may be controlled by the AGC loop to amplify or reduce the intensity of light transmitted by the pulse oximeter to a level suitable for use by the measurement circuitry of the pulse oximeter. For example, the AGC loop may apply gain to the LED light pulses transmitted by the pulse oximeter into a patient to amplify or reduce the intensity of light transmitted to a level suitable for reception by the sensor elements of the pulse oximeter.

SUMMARY

Various embodiments provide methods for measurement quality of one or more measurements from one or more sensors. As an example, the systems, methods, and devices of the various embodiments may include a sensor (e.g., a pulse oximeter, an ultrasound sensor, a bioimpedance sensor, etc.) configured to track an alternating current (AC) component of a waveform of measured signals (e.g., optical signals, acoustic signals, bioimpedance signals, etc.) received by the sensor and take an action based on a characteristic of the AC component of the waveform. Various embodiments provide methods for tracking sensor measurement quality.

Various embodiments may include obtaining, at a processor, a gain of a first signal generated by the one or more sensors, wherein the one or more sensors are positioned on a subject's body, determining, at the processor, a gain of a second signal generated by the one or more sensors, and generating, at the processor, a contact quality based on a comparison of the first signal's gain and the second signal's gain, wherein the contact quality corresponds to a level of contact between the one or more sensors and the subject's body. In some embodiments, generating a contact quality based on the comparison of the first signal's gain and the second signal's gain may include comparing the first signal's gain, the second signal's gain, and one or more thresholds. Some embodiments may include adjusting one or more sensing modalities of the one or more sensors based on the contact quality. In some embodiments, a low contact quality may indicate improper placement of the one or more sensors, movement of the subject, or any combination thereof. Some embodiments may include filtering one or more measurements from the one or more sensors based on a comparison of the contact quality and at least one of a second threshold, wherein the one or more measurements are associated with the second signal. In some embodiments, the obtaining, determining, and generating may be performed after changes in gain applied have stabilized to account for the subject's body skin type and color.

Various embodiments may include determining, at a processor, a peak-to-peak voltage of a received signal from the one or more sensors, and generating, at the processor, a contact quality based on the peak-to-peak voltage and one or more thresholds, wherein the contact quality corresponds to a level of contact between the one or more sensors and the subject's body. Some embodiments may include filtering one or more measurements from the one or more sensors associated with the received signal based on a comparison of the contact quality and one or more thresholds. In some embodiments, the contact quality may indicate improper placement of the one or more sensors, movement of the subject, or any combination thereof.

Some embodiments may include a pulse oximeter having one or more sensors and a processor configured to perform operations of the methods described above. In some embodiments the pulse oximeter may be integrated in an electronic patch.

BRIEF DESCRIPTION OF THE DRAWINGS

The accompanying drawings, which are incorporated herein and constitute part of this specification, illustrate embodiments of the invention, and together with the general description given above and the detailed description given below, serve to explain the features of the invention.

DETAILED DESCRIPTION

Figure 1:
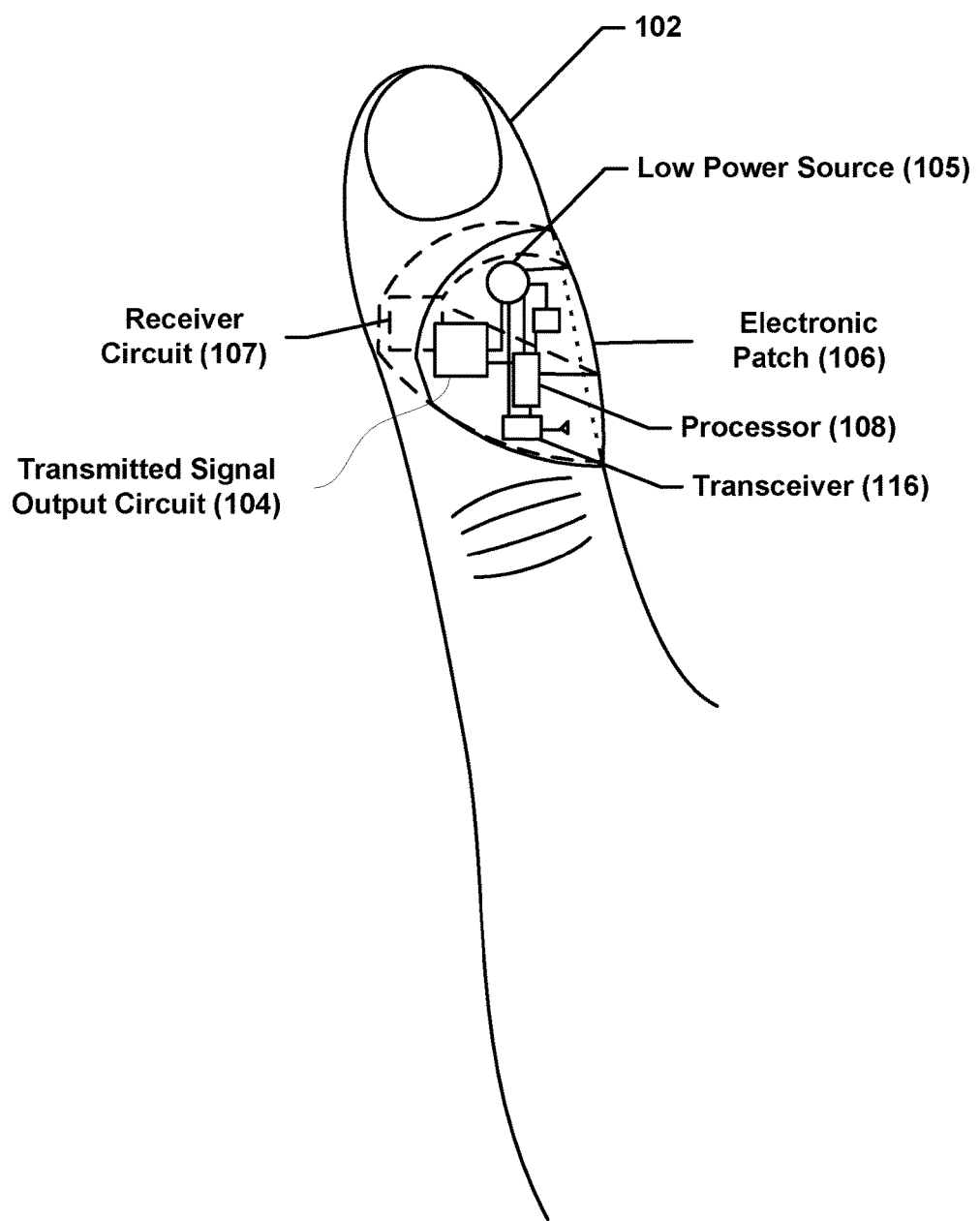
FIG. 1 is a component block diagram illustrating an electronic patch including a pulse oximeter placed on a patient suitable for implementing various embodiments.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The terms "computing device" are used herein to refer to any one or all of cellular telephones, smart-phones, web-pads, tablet computers, Internet enabled cellular telephones, wireless local area network (WLAN) enabled electronic devices, laptop computers, personal computers, smart apparel, vehicle (e.g., aircraft, train, bus, motorcycle, truck, automobile, etc.) computer systems, smart furniture, and similar electronic devices equipped with at least a processor and configured to communicate with a pulse oximeter as described herein.

The variance in the AC and DC level of the received and/or transmitted signal may be caused by improper placement of a pulse oximeter and/or by movement of the patient after a pulse oximeter is placed on the patient. For example, improper placement of a pulse oximeter may result in signal quality for the received signal being below a minimum threshold for acceptable readings. As another example, movement of the patient may cause one or more sensors of the pulse oximeter, such as the sensor elements of the pulse oximeter, to lose contact with the patient's skin resulting in the signal quality for the received signal falling below a minimum threshold for acceptable readings. Due to this impact on the quality for the received signal, improper placement and/or movement of the patient may result in degradation of the blood oxygen level measurements and heart rate measurements by a pulse oximeter. The risk of improper placement and separation of the sensor from the skin due to patient movements on a wearable pulse oximeter (e.g., an electronic patch including a pulse oximeter, smart apparel including a pulse oximeter, hospital ID band including a pulse oximeter, head gear including a pulse oximeter, etc.) is greater than that of wired stationary pulse oximeter devices. Additionally, a risk of separation of the sensor from the skin may be greater for a wearable pulse oximeter than for a wired stationary pulse oximeter device because a wearable pulse oximeter may be placed on portions of a patient's skin that are covered by hair and/or that are excessively oily, dry, etc. While a wired stationary pulse oximeter device may be placed on an area of the patient's skin with no hair (e.g., a finger tip) in a hospital setting, a wearable pulse oximeter may be awkward to wear on portion of skin with no hair (e.g., a finger), may be integrated into a device that measures multiple vital signs necessitating alternative placements on the patient's skin, may be required to be placed so as to feel natural to the patient and not impede the patient's movement, and/or to may be placed to meet the patient's fashion preferences. Thus, methods for accounting for improper placement, patient skin conditions, and/or patient movements may enable pulse oximeters to be integrated into wearable form factors, such as electronic patches, smart apparel, hospital ID bands, sports helmets, sports wrist or head bands, etc.

The systems, methods, and devices of various embodiments may include determining a gain applied to a current signal of one or more sensors, accessing a previous signal of the one or more sensors, determining a contact quality (e.g., a level of contact) based on the current signal and a previous signal, and transmitting the contact quality. As examples, the level of contact may be a value representing the proximity of the sensors to the subject's body and/or artery, the level of contact may be a value representing the amount of movement of the user, the level of contact may be a value representing the accuracy of the placement, etc. Various embodiments may be applied to or used in conjunction with a variety of sensors. A non-limiting example of a sensor that may implement various embodiments is a pulse oximeter configured to track an AC and/or DC component of a waveform of a measured parameter (e.g., light of various wavelengths, sound waveforms, bioimpedance signals, etc.) received by the pulse oximeter, also referred to as the received signal. Using the example of a pulse oximeter, various embodiments may track an AC and/or DC component of a waveform of light generated by the pulse oximeter, also referred to as the transmitted signal, and filter the measurement results of the pulse oximeter based on a characteristic of the AC and/or DC component of the waveforms. Transmitted and/or received signals with characteristics that are discontinuous (i.e., transmitted and/or received signals with characteristics that experience a change that is greater than a selected allowable value from a last transmitted and/or received signal) may be indicative of erroneous or poor quality readings by the pulse oximeter, such as erroneous or poor quality readings caused by patient movement and/or misplacement of the pulse oximeter. Transmitted and/or received signals with a characteristic above or below an acceptable range may be indicative of erroneous or poor quality readings by the pulse oximeter, such as erroneous or poor quality readings caused by misplacement of the pulse oximeter.

In some embodiments, blood oxygen level measurements and/or pulse measurements based on transmitted and/or received signals with a discontinuous characteristic and/or a characteristic above or below an acceptable range may be indicated by the pulse oximeter. In some embodiments, blood oxygen level measurements and/or pulse measurements based on transmitted and/or received signals with a discontinuous characteristic and/or a characteristic above or below an acceptable range may be filtered out and not returned as valid measurements by the pulse oximeter. In some embodiments, blood oxygen level measurements and/or pulse measurements based on transmitted and/or received signals with a discontinuous characteristic and/or a characteristic above or below an acceptable range may be both indicated by the pulse oximeter and filtered out. The indication and/or filtering of the blood oxygen level measurements and/or pulse measurements based on transmitted and/or received signals with a discontinuous characteristic and/or a characteristic above or below an acceptable range may enable a pulse oximeter to account for improper placement and/or movements of the patient.

Various embodiments include an electronic patch having a pulse oximeter connected to a processor. In such embodiments, the processor, which may be specialize hardware, a programmable processor configured with processor executable instructions or a combination of specialized hardware and programmable processor(s), may be configured to control the operation of the pulse oximeter based at least in part on one or more waveform characteristics of the waveform of measured light received by the pulse oximeter, also referred to as the received signal, and/or one or more waveform characteristics of the waveform of the light transmitted by the pulse oximeter, also referred to as the transmitted signal. In various embodiments, waveform characteristics that may be monitored or used for controlling operation of the pulse oximeter may include one or more of gain applied to the received signal, gain applied to the transmitted signal, and peak-to-peak voltage of the received signal. In various embodiments, the processor may filter out one or more blood oxygen level measurement and/or one or more pulse measurement based on waveform characteristics associated with the transmitted and/or received signal used to generate the blood oxygen level measurements and/or pulse measurements. In various embodiments, the processor may be configured to indicate a quality of the blood oxygen level measurements and/or pulse measurements to a remote device, such as a smart phone, based on the waveform characteristics of the transmitted and/or received signal used to generate the blood oxygen level measurements and/or pulse measurements. In various embodiments, the electronic patch may further include a coin cell battery or other low power source that provides power to the pulse oximeter.

When a subject first wears a device there may be significant changes in the signals as the device accounts for a subject's body skin type and color until the gain applied by the device to the received signal stabilizes. In various embodiments, the operations to determine measurement quality of one or more measurements from one or more sensors discussed herein may be performed after the signals associated with accounting for a subject's body skin type and color have stabilized. In this manner, various embodiments may address signals associated only with dealing with movement of the sensors, rather than signals accounting for skin type and color.

FIG. 1 illustrates an embodiment electronic patch 106 including a sensor placed on a patient 102, such as on a skin surface of a finger of a patient 102. In various embodiments, an electronic patch 106 may be flexible and resilient so that placement and removal of the electronic patch 106 from the patient 102 does not damage the electronic patch 106. In the example illustrated in FIG. 1, the electronic patch 106 includes a pulse oximeter circuit comprised of an transmitted signal output circuit 104 (e.g., a circuit including one or more light generator element, such as one or more LEDs, that output light, one or more sound generator elements that output sound, etc.) and a receiver circuit 107 (e.g., a circuit including one or more phototransistor, a circuit including one or more microphones, etc.) configured to measure signals transmitted through the patient's skin and tissue emitted by the transmitted signal output circuit 104. The transmitted signal receiver circuit 107, alone or in combination with other elements (e.g., the light output circuit 104) of the pulse oximeter and/or electronic patch 106 may constitute one or more sensors of the pulse oximeter.

The processor 108 may be connected to the transmitted signal output circuit 104 and receiver circuit 107. The processor 108, which may be specialize hardware, a programmable processor configured with processor executable instructions or a combination of specialized hardware and programmable processor(s), may be configured to control the operations of and/or receive measurements from the pulse oximeter (e.g., the transmitted signal output circuit 104 and/or the receiver circuit 107). In some embodiments, the processor 108 may be configured with internal circuitry and/or processor executable instructions to perform signal processing operations, such as filtering a received signal, applying automatic gain control to a transmitted and/or received signal, converting a received signal from an analog to a digital signal, and/or any other type signal processing operations. In some embodiments, a filtering circuit (not shown) may be connected between the processor 108 and the receiver circuit 107, and the processor may be configured to control the filtering circuit to perform signal processing operations. For example, the processor may control the filtering circuit to perform operations such as filtering a received signal, applying automatic gain control to a transmitted and/or received signal, converting a received signal from an analog to a digital signal, and/or any other type signal processing operations. In such an embodiment, the filtered received signal may be output from the filter circuit to the processor 108.

In an embodiment, the processor 108 may be further configured to determine the patient's 102 blood oxygen level and/or pulse based on signals received from the pulse oximeter (e.g., the transmitted signal output circuit 104 and/or light receiver circuit 107). In an embodiment, the transmitted signal output circuit 104, the receiver circuit 107, and/or the processor 108 may be connected to a low power source 105, such as a coin cell battery.

The processor 108 may intermittently turn the pulse oximeter (e.g., the transmitted signal output circuit 104 and/or the receiver circuit 107) on and off to reduce the total amount of current drawn from the low power source 105 compared with continually leaving the pulse oximeter (e.g., the transmitted signal output circuit 104 and/or the receiver circuit 107) on. Turning the pulse oximeter (e.g., the transmitted signal output circuit 104 and/or the receiver circuit 107) on intermittently may extend the life of the low power source 105, such as a coin cell battery, compared to the life of the low power source 105 that could be achieved with the pulse oximeter always on.

The electronic patch 106 may also include a transceiver 116 connected to an antenna and the processor 108 and the low power source 105. Using the transceiver 116, the processor 108 may establish wireless connections (e.g., Bluetooth® connections) and exchange data with remote devices, such as a smart phone. The transceiver 116 is an example of one type of wireless connection device suitable for use in the various embodiments, and other configurations of receivers and/or transmitters may be substituted for transceiver 116 to provide transmission and/or reception capabilities to the processor 108 as needed for various different use cases for the electronic patch 106.

Figure 2:
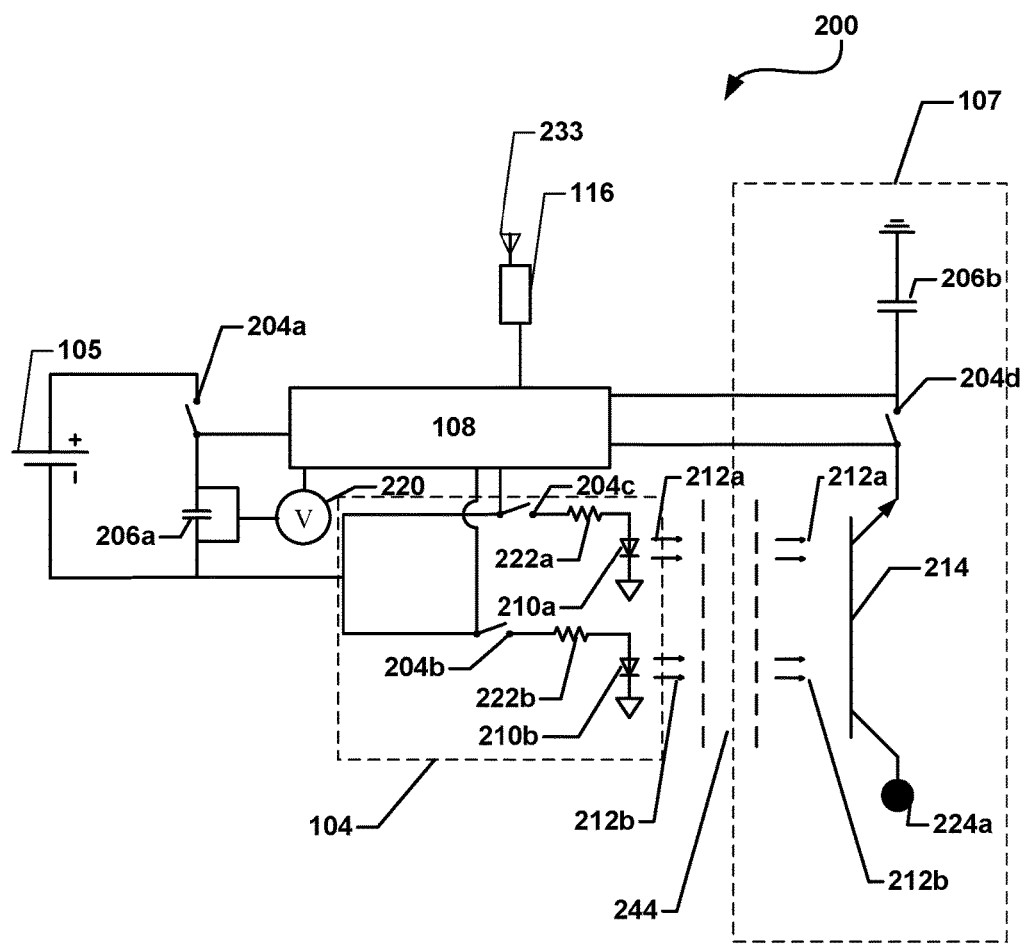
FIG. 2 is a circuit diagram illustrating a circuit for a pulse oximeter that may be suitable for inclusion on an electronic patch implementing various embodiments.

FIG. 2 is a circuit diagram illustrating an embodiment circuit 200 for a pulse oximeter. While FIG. 2 illustrates components of a pulse oximeter, other types of sensors that may use various embodiments may include the same or similar components. In the embodiment illustrated in FIG. 2, the circuit 200 may be integrated into an electronic patch worn by a patient, such as the electronic patch 106 described above. A low voltage power source may power the processor 108 or the processor may be powered by a separate power source (not shown). The low power source 105 powers the capacitor 206a when the switch 204a is closed. The switch may be located anywhere on the loop containing the low power source 105 and switch 204a, provided that the switch can electrically separate the low power source 105 and switch 204a. The processor 108 may control when the switch 204a opens or closes. For example, the processor 108 may close the switch 204a to allow the capacitor 206a to collect electric charge. The charge on the capacitor 206a may correspond via a known relationship to the voltage across the capacitor 206a. The voltage across the capacitor 206a may be monitored by a voltmeter 220. The voltmeter 220 may report the measured voltage to processor 108.

When the voltage across capacitor 206a reaches a predetermined limit, the processor 108 may open the switch 204a at an appropriate time to provide power to a transmitted signal output circuit 104 to cause the transmitted signal output circuit 104 to generate the transmitted signal (e.g., light of various wavelengths, sound waveforms, bioimpedance signals, etc.). As an example, the transmitted signal output circuit 104 may include switches 204b and 204c and a red LED 210a and infrared LED 210b. The processor 108 may close the switches 204b, 204c to allow charge to flow from the capacitor 206a to the red LED 210a and the infrared LED 210b. The switches 204b and 204c may be closed consecutively to measure the different wavelength absorption rates in quick succession. The switches 204b, 204c may remain open while the capacitor 206a is charging to prevent unnecessary drain on the low power source 105.

Resistors 222a, 222b may be connected in series with a red LED 210a and an infrared LED 210b to control the current passing through each LED 210a, 210b. The resistors 222a, 222b may have the same or different resistances than each other. The resistors 222a, 222b may provide greater control on the allocation of current from the capacitor 206a, thus helping to eliminate the need for higher-current power supplies.

In an embodiment, the switches 204b, 204c may be closed by the processor 108 to provide charge from the capacitor 206a to the red LED 210a and infrared LED 210b for a period of time to cause the LEDs 210a and 210b to emit red light 212a and infrared light 212b, respectively. After the period of time, the switches 204b, 204c may be opened by the processor 108 to isolate the LEDs 210a and 210b from the capacitor 206a, interrupting the flow of current from the capacitor 206a to the LEDs 210a and 210b, and thus stopping the emission of light from the LEDs 210a and 210b. In this manner, light bursts may be generated from the red LED 210a and infrared LED 210b, and the current draw of the circuit 200 may be minimized by only turning the red LED 210a and infrared LED 210b on for brief periods of time.

When sufficient current passes through the red LED 210a and infrared LED 210b, the LEDs emit red light 212a and infrared light 212b, respectively. The light 212a, 212b propagates through a body part 244, such as a fingertip or earlobe. The amount of light absorbed by the body part 244 may be a function of the amount of oxygen in the blood and the amount of blood in the body part 244 at the time of sampling. A body part 244 with a relatively large amount of oxygen will tend to absorb more infrared light 212b and less red light 212a. A body part 244 with a relatively small amount of oxygen will tend to absorb less infrared light 212b and more red light 212a.

After passing through the body part 244, the red light 212a and infrared light 212b may be measured by a sensor, such as a photodetector 214, phototransistor or a light sensor, of a receiver circuit 107. The receiver circuit 107 may include the photodetector 214, a switch 204d, and a capacitor 206b. Analysis by the processor 108 of the absolute amplitude of the detected light signal, as well as the relative amplitudes of the detected red light and detected infrared light, may reveal various properties of the blood, such as the pulse profile and the amount of oxygen in the blood.

The photodetector 214 may be powered by a voltage source 224a. The processor 108 may control a switch 204d that regulates current from the voltage source 224a to the photodetector 214. When the switch 204d is closed, the photodetector 214 may transfer data to the processor 108. The processor 108 may synchronize the opening and closing of the switch 204d with the switches 204a, 204b, 204c such that the switch 204d is only closed when the photodetector 214 is receiving light. Power demand may be reduced further by leaving the switch 204d open when the photodetector is not receiving useful data. When the switch 204d is closed, current may flow from the photodetector 214 to the capacitor 206b and be stored in the capacitor 206b at the input of the processor 108.

An A/D converter of the processor 108 may measure the voltage at the capacitor 206b. An AGC loop of the processor 108 may amplify or reduce the voltage amplitude of the measured voltage before the voltage is passed to the A/D converter.

In an embodiment, the on periods of the red LED 210a and infrared LED 210b may be synchronized with the opening and closing of switch 204d by processor 108. The processor 108 may close the switch 204d to allow the photodetector 214 to start integrating its received signal just before the red LED 210a and infrared LED 210b are turned on by discharging the capacitor 206a, and may control the AGC loop and A/D converter to take a voltage measurement as soon as the red LED 210a and infrared LED 210b are off. In an embodiment, the photodetector 214 may be a single device and may include two separate detectors tuned separately for each wavelength of light in use. The digital output of the A/D converter may be the output of the light receiver circuit 107, which may be analyzed by the processor 108 as measurements of the blood oxygen level.

A transceiver 116 connected to an antenna 233 may be coupled to the processor 108 and configured to establish wireless connections, e.g., Bluetooth® connections, such as Bluetooth® Low Energy (Bluetooth LE) connections and exchange data with remote devices (e.g., a smartphone). The transceiver 116 is an example of one type of wireless connection device suitable for use in the various embodiments, and other configurations of receivers and/or transmitters may be substituted for transceiver 116 to provide transmission and/or reception capabilities to the processor 108 as needed for various different use cases for the circuit 200.

While various embodiments are discussed with reference to an electronic patch including a pulse oximeter, such as electronic patch 106, pulse oximeters may be integrated into other form factors, such as smart apparel (e.g., smart shoes, smart shirts, smart wrist bands, smart necklaces, smart pants, etc.), smart furniture, vehicle (e.g., commercial and/or military aircraft, trains, buses, trucks, motorcycles, etc.) components (e.g., seats, steering wheels, arm rests, etc.), stretchers, ambulances, beds, hospital ID bands, sports equipment (e.g., pads, handle bars, grips, etc.), head gear (helmets, head bands, etc.), stationary medical readers, etc. Thus, the various embodiments may be applicable to any form factor including a pulse oximeter.

Figure 3:
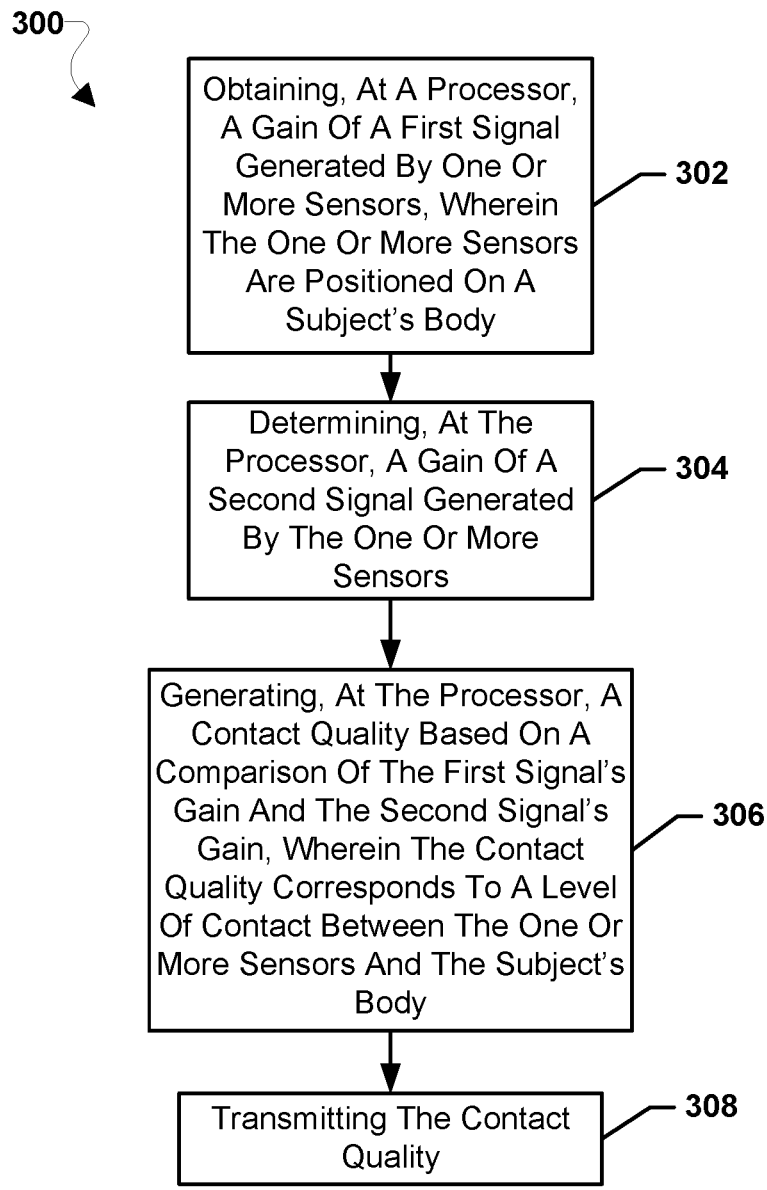
FIG. 3 is a process flow diagram illustrating a method for measurement quality of one or more measurements from one or more sensors.

FIG. 3 illustrates an embodiment method 300 for measurement quality of one or more measurements from one or more sensors. In an embodiment, the operations of method 300 may be performed by a processor (e.g., processor 108) of an electronic patch including a pulse oximeter, such as patch 106.

In block 302, the processor may perform operations including obtaining a gain of a first signal generated by one or more sensors, wherein the one or more sensors are positioned on a subject's body. For example, the processor may obtain the first signal by accessing a previous signal of the one or more sensors by retrieving data associated with a previous signal from a memory available to the processor.

In block 304, the processor may perform operations including determining a gain of a second signal generated by the one or more sensors. For example, the second signal may be a current signal, such as the most recent waveform of the transmitted signal by the pulse oximeter output from a signal generator element (e.g., an LED), also referred to herein as the transmitted signal, or may be the most recent waveform of measured signals (e.g., light, sound, bioimpedance, etc.) received by a light sensor element of the pulse oximeter (e.g., a phototransistor), also referred to as the received signal. An AGC loop may amplify or reduce the transmitted signal and/or the received signal, and the processor may determine the gain applied to the current signal by tracking the gain applied to amplify or reduce the voltage amplitude of the transmitted and/or received signal of the pulse oximeter, such as the gain applied by an AGC loop to the AC and/or DC component of the transmitted and/or received signal. The gain applied may be a value associated with an AGC loop, such as an amplification variable value, a number of bit counts, etc. As part of determining the gain applied to the current signal, the gain applied may be stored in a memory available to the processor. In this manner, a history of gains applied to one or more signals may be tracked by the processor.

In block 306, the processor may perform operations including generating a contact quality based on a comparison of the first signal's gain and the second signal's gain, wherein the contact quality corresponds to a level of contact between the one or more sensors and the subject's body. As examples, the level of contact may be a value representing the proximity of the sensors to the subject's body and/or artery, the level of contact may be a value representing the amount of movement of the user, the level of contact may be a value representing the accuracy of the placement, etc. Some embodiments may include determining the contact quality based on the current signal and the previous signal by comparing the current signal to the previous signal and determining the contact quality based on the comparison of the current signal to the previous signal. Some embodiments may include comparing the current signal to the previous signal by comparing the current signal, the previous signal, and one or more thresholds. Some embodiments may include determining the contact quality based on the current signal, the previous signal and one or more threshold by determining the contact quality is high based on the current signal and previous signal meeting or exceeding one or more thresholds. Some embodiments may include determining the contact quality based on the current signal, previous signal, and one or more thresholds by determining the contact quality is low based on the current signal and previous signal meeting or exceeding one or more thresholds. Some embodiments may further include determining a quality level of the one or more sensor measurements based on the current signal and the previous signal, and transmitting the quality level.

In some embodiments, the processor may determine a change in gain between the current signal and a previous signal of the pulse oximeter. The processor may determine a change in gain between the current signal and a previous signal by retrieving the value of the gain applied to a previous signal, such as the gain applied to a previously transmitted and/or received signal, from a memory available to the processor and subtracting the determined gain of the current signal from the gain applied to the previous signal. The absolute value of the difference between the determined gain of the current signal and the gain applied to the previous signal may be the change in gain. Alternatively, the absolute value of the difference between the determined gain of the current signal and the gain applied to the previous signal over the time difference between the current signal and the previous signal may be the change in gain. In this manner, the change in gain may be an indication of the rate of change in gain. The gain applied to the previous signal may be the value of the gain applied to the most recent transmitted and/or received signal. Additionally, the gain applied to the previous signal may be the average value of the gain applied to a plurality of previously transmitted and/or received signals.

The processor may determine whether the change in gain is discontinuous. Discontinuous gain change may be changes in gain that are greater than a selected allowable value. The selected allowable value may be an absolute value associated with a maximum allowable difference between the gain applied to the current signal and the gain applied to the previous signal. Additionally, the selected allowable value may be a maximum allowable rate of change in gain applied to the current signal. The determined change in gain may be compared to the selected allowable value to determine whether the change in gain is discontinuous. When the change in gain is at or below the selected allowable value, the change in gain may be continuous. Continuous gain may indicate that the AGC loop may be locked, which may indicate acceptable or good quality readings by the pulse oximeter, such as acceptable or good quality readings caused by acceptable contact with a patient's skin and/or proper placement of the pulse oximeter. When the change in gain is above the selected allowable value, the change in gain may be discontinuous. Discontinuous gain change may indicate that the AGC loop may be unlocked, which may indicate erroneous or poor quality readings by the pulse oximeter, such as erroneous or poor quality readings caused by patient movement and/or misplacement of the pulse oximeter.

In response to determining that the gain applied is continuous, the processor may indicate that the pulse oximeter measurement(s) associated with the current signal is/are high quality. Indicating that the pulse oximeter measurement(s) associated with the current signal is/are high quality may include sending an indication to a remote device, such as a smart phone, that the blood oxygen level measurements and/or the pulse measurements determined based on the transmitted and/or received signal with the applied continuous gain are high quality measurements. For example, the quality indication may be sent over a Bluetooth® link to the remote devices, such as a Bluetooth Low Energy (LE) link. The indication that that the blood oxygen level measurements and/or the pulse measurements are high quality measurements may be sent with the transmission of the blood oxygen level measurements and/or the pulse measurements themselves and/or as a separate message. The indications sent by the processor that the blood oxygen level measurements and/or the pulse measurements are high quality measurements may be indications of a scale of the quality of the measurements determined by the processor. As an example, the amount by which the change in gain is at or below the allowable value may be correlated by the processor with a scale, such as 1-10, and the processor may send the scale value as the indication to the remote device.

In response to determining that the gain applied is discontinuous, the processor may indicate that the pulse oximeter measurement(s) associated with the current signal is/are low quality. Indicating that the pulse oximeter measurement(s) associated with the current signal is/are low quality may include sending an indication to a remote device, such as a smart phone, that the blood oxygen level measurements and/or the pulse measurements determined based on the transmitted and/or received signal with the applied gain above or below the acceptable gain range are low quality measurements. For example, the quality indication may be sent over a Bluetooth® link to the remote device, such as a Bluetooth LE link. The indication that that the blood oxygen level measurements and/or the pulse measurements are low quality measurements may be sent with the transmission of the blood oxygen level measurements and/or the pulse measurements themselves and/or as a separate message. The indications sent by the processor that the blood oxygen level measurements and/or the pulse measurements are low quality measurements may be indications of a scale of the quality of the measurements determined by the processor. As an example, the amount by which the change in gain above the allowable value may be correlated by the processor with a scale, such as 1-10, and the processor may send the scale value as the indication to the remote device.

In block 308, the processor may perform operations including transmitting the contact quality. In some embodiments, processor may transmit the contact quality to a remote device, such as a smart phone. In some embodiments, the processor may also transmit blood oxygen level measurements and/or pulse measurements determined based on the transmitted and/or signal to a remote device, such as a smart phone.

Some embodiments may further include determining a quality level of the one or more sensor measurements based on the current signal and the previous signal, and transmitting the quality level. Some embodiments may further include adjusting one or more sensing modalities of the one or more sensors based on the gain applied. In some embodiments the quality level may indicate improper placement of the one or more sensors, movement of the subject, or any combination thereof.

In some embodiments, the processor may determine whether the gain applied is within an acceptable gain range. In this determination, the processor may compare the gain applied to an acceptable gain range or set of thresholds in order to determine whether the gain applied is within an acceptable gain range. The acceptable gain range may be a range of gain values extending from a minimum gain value to a maximum gain value. Alternatively, the acceptable gain range may be defined by a minimum threshold value and a maximum threshold value. The minimum gain value and/or the maximum gain value may be values associated with the AGC loop, such as an amplification variable value, a number of bit counts, etc. The acceptable gain range may be selected such that the amplified or reduced transmitted and/or received signal resulting from the application of the AGC may have a voltage within a threshold input level of an A/D converter of the pulse oximeter.

In response to determining that the gain applied is within the acceptable gain range, the processor may indicate that the pulse oximeter measurement(s) associated with the current signal is/are high quality. Indicating that the pulse oximeter measurements associated with the current signal are high quality may include sending an indication to a remote device, such as a smart phone, that the blood oxygen level measurements and/or the pulse measurements determined based on the current signal with the applied gain within the acceptable gain range are high quality measurements.

In response to determining that the gain applied is above or below the acceptable gain range, the processor may indicate that the pulse oximeter measurement(s) associated with the current signal is/are low quality. Indicating that the pulse oximeter measurements associated with the current signal are low quality may include sending an indication to a remote device, such as a smart phone, that the blood oxygen level measurements and/or the pulse measurements determined based on the transmitted and/or received signal with the applied gain above or below the acceptable gain range are low quality measurements. Such an indication that the pulse oximeter measurements are low quality may be sent with the transmission of the pulse oximeter measurements or sent as a separate message. A change in gain at or above the selected allowable value may indicate patient movement and/or misplacement of the pulse oximeter that may impact the blood oxygen level measurements and/or the pulse measurements.

In an embodiment, the processor may optionally adjust the transmitted light based on the gain applied. Adjusting the transmitted light based on the gain may include adjusting an intensity of light transmitted by the pulse oximeter based on the gain applied. For example, adjusting the transmitted light based on the gain may include the processor of the pulse oximeter varying the amount of light emitted by a red LED and/or an infrared LED so that a suitable amount of measured light is received (i.e., the received signal has a voltage amplitude above a minimum amount and/or below a maximum amount). Adjusting the transmitted light may be optional because the transmitted light intensity may not be adjusted in each measurement cycle. For example, the light intensity may only be increased or decreased every ten or twenty measurement cycles. Additionally, adjusting the transmitted light may be optional because the intensity of the transmitted light may not be adjustable for all pulse oximeters.

In some embodiments, the processor may determine whether the pulse oximeter's selected power state is indicated as "on". By determining whether the pulse oximeter's selected power state is indicated as "on", the pulse oximeter may be turned on and off intermittently to reduce the total amount of current drawn from a power source, such as a low power source, compared with continually leaving the pulse oximeter on. The selected power state may be indicated in any manner, such as by a flag bit setting in a memory location indicting whether the pulse oximeter is to be powered on or off. In response to determining that the pulse oximeter selected power state is not on (e.g., is "off"), the processor may power off the pulse oximeter. In response to determining that the pulse oximeter selected power state is on, the processor may power on the pulse oximeter.

Some embodiments may further include filtering one or more measurements from the one or more sensors associated with the current signal based on a comparison of the contact quality and one or more thresholds. For example, in response to determining that the change in gain is discontinuous, the processor may filter the pulse oximeter measurements associated with the current signal. In various embodiments, filtering the pulse oximeter measurements associated with the transmitted and/or received signal may including filtering out all blood oxygen level measurements and/or pulse measurements determined based on transmitted and/or received signals with a discontinuous change in gain. In various embodiments, filtering out the pulse oximeter measurements may include not transmitting blood oxygen level measurements and/or pulse measurements determined based on the transmitted and/or received signal exhibiting a discontinuous change in gain. By avoiding transmission of blood oxygen level measurements and/or pulse measurements determined based on the transmitted and/or received signal with a discontinuous change in gain applied, the pulse oximeter may avoid transmission of degraded measurements and may avoid current drain on the power source. As another example, in response to determining that the gain applied is above or below the acceptable gain range, the processor may filter the pulse oximeter measurements associated with the current signal. In various embodiments, filtering the pulse oximeter measurements associated with the transmitted and/or received signal may including filtering out all blood oxygen level measurements and/or pulse measurements determined based on transmitted and/or received signals with the applied gain outside the acceptable gain range. In various embodiments, filtering out the pulse oximeter measurements may include not transmitting blood oxygen level measurements and/or pulse measurements determined based on the transmitted and/or received signal with applied gain above or below the acceptable gain range. By avoiding transmission of blood oxygen level measurements and/or pulse measurements determined based on the transmitted and/or received signal with the applied gain outside the acceptable gain range, the pulse oximeter may avoid transmission of degraded measurements and may avoid current drain on the power source.

The method 300 may be performed repetitively, such as with each measurement cycle.

When a subject first wears a device there may be significant changes in the signals as the device accounts for a skin type and color of the subject's body until the gain applied by the device to the received signal stabilizes. In an embodiment, the operations of the method 300 may be performed after the signals associated with accounting for the skin type and color of the subject's body have stabilized. In this manner, the operations of method 300 may address signals associated only with dealing with movement of the sensors, rather than signals accounting for skin type and color. For example, upon placement of a device on the subject, the processor may determine whether the changes in gain applied have stabilized to account for the subject's body skin type and color. In response to determining that the changes in gain applied have stabilized to account for the subject's skin type and color, the processor may perform the operations of block 302 of the method 300.

Figure 4:
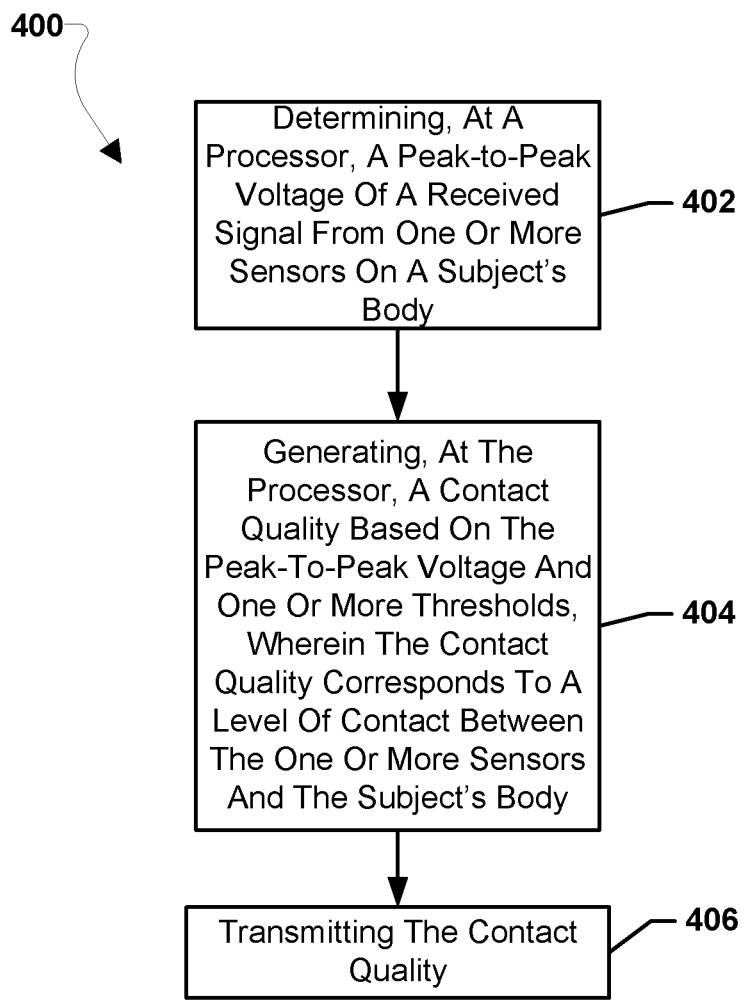
FIG. 4 is a process flow diagram illustrating a method for determining measurement quality of one or more measurements from one or more sensors.

FIG. 4 illustrates an embodiment method 400 for method for determining measurement quality of one or more measurements from one or more sensors. In an embodiment, the operations of method 400 may be performed by a processor (e.g., processor 108) of an electronic patch including a pulse oximeter, such as patch 106.

In block 402, the processor may perform operations including determining a peak-to-peak voltage of a received signal from one or more sensors. For example, the processor may determine the peak-to-peak voltage of a received signal that is an output of a light sensor of the pulse oximeter. The received signal may be a waveform of an output from a light sensor element of the pulse oximeter, such as a phototransistor. In various embodiments, the processor of a pulse oximeter may track the peak-to-peak voltage of an AC component of the received signal. The peak-to-peak voltage may be tracked as a value, such as a voltage value, a number of bit counts, etc.

In block 404, the processor may perform operations including generating a contact quality based on the peak-to-peak voltage and one or more thresholds, wherein the contact quality corresponds to a level of contact between the one or more sensors and the subject's body. As examples, the level of contact may be a value representing the proximity of the sensors to the subject's body and/or artery, the level of contact may be a value representing the amount of movement of the user, the level of contact may be a value representing the accuracy of the placement, etc. Some embodiments may include determining the contact quality based on the peak-to-peak voltage and one or more thresholds by comparing the peak-to-peak voltage and one or more thresholds and determining the contact quality based on the comparison of the peak-to-peak voltage and one or more thresholds. In some embodiments, the processor may determine whether the peak-to-peak voltage is within an acceptable peak-to-peak voltage range. The processor may compare the peak-to-peak voltage of the AC component to an acceptable peak-to-peak voltage range. The acceptable peak-to-peak voltage range may be a range of peak-to-peak voltages extending from a minimum voltage to a maximum voltage. Alternatively, the acceptable peak-to-peak voltage range may be defined by a minimum threshold value and a maximum threshold value. The minimum voltage and/or the maximum voltage may be various type values, such as a voltage value, a number of bit counts, etc. In an embodiment, the acceptable peak-to-peak voltage range may be a minimum threshold value, and acceptable peak-to-peak voltages may include any peak-to-peak voltages above the minimum threshold value without regard to a maximum voltage threshold value.

Some embodiments may further include filtering one or more measurements from the one or more sensors associated with the received signal based on a comparison of the contact quality and one or more thresholds. In some embodiments, in response to determining that the peak-to-peak voltage is above or below the acceptable peak-to-peak voltage range, the processor may filter the pulse oximeter measurements associated with the received signal. In some embodiments, filtering the pulse oximeter measurements associated with the received signal may including filtering out all blood oxygen level measurements and/or pulse measurements determined based on the received signal with the peak-to-peak voltage above or below the acceptable peak-to-peak voltage range. In some embodiments, filtering out the pulse oximeter measurements may include not transmitting blood oxygen level measurements and/or pulse measurements determined based on the received signal with peak-to-peak voltage above or below the acceptable peak-to-peak voltage range. By avoiding transmission of blood oxygen level measurements and/or pulse measurements determined based on the received signal with the peak-to-peak voltage outside the acceptable peak-to-peak voltage range, the pulse oximeter may avoid transmission of degraded measurements and may avoid current drain on a coin cell battery, or other low power source, that may power the pulse oximeter. In some embodiments, in response to determining that the peak-to-peak voltage is within the acceptable peak-to-peak voltage range, the processor may take no action to block the recording or transmission of the data, such as to a remote device (e.g., a smartphone).

In block 308, perform the operations of like numbered blocks of method 300 described with reference to FIG. 3 to transmit the contact quality.

Some embodiments may further include determining a quality level of the one or more sensor measurement based on the received signal, and transmitting the quality level. In some embodiments the quality level may indicate improper placement of the one or more sensors, movement of the subject, or any combination thereof. In response to determining that the peak-to-peak voltage is within the acceptable peak-to-peak voltage range, the processor may indicate that the pulse oximeter measurement(s) associated with the received signal is/are high quality. Indicating that the pulse oximeter measurements associated with the received signal are high quality may include sending an indication to a remote device, such as a smart phone, that the blood oxygen level measurements and/or the pulse measurements determined based on the received signal with the with the peak-to-peak voltage within the acceptable peak-to-peak voltage range are high quality measurements. As an example, the amount by which the peak-to-peak voltage is within the acceptable peak-to-peak voltage range may be correlated by the processor with a scale, such as 1-10, and the processor may send the scale value as the indication to the remote device. In response to indicating that the pulse oximeter measurements are high quality, the processor may determine the peak-to-peak voltage of the received signal for a next measurement cycle.

In response to determining that the peak-to-peak voltage is outside the acceptable peak-to-peak voltage range, the processor may indicate that the pulse oximeter measurement(s) associated with the received signal is/are low quality. Indicating that the pulse oximeter measurements associated with the received signal are low quality may include sending an indication to a remote device, such as a smart phone, that the blood oxygen level measurements and/or the pulse measurements determined based on the received signal with the peak-to-peak voltage above or below the acceptable peak-to-peak voltage are low quality measurements. As an example, the amount by which the peak-to-peak voltage is outside the acceptable peak-to-peak voltage range may be correlated by the processor with a scale, such as 1-10, and the processor may send the scale value as the indication to the remote device.

The method 400 may be performed repetitively, such as with each measurement cycle Various embodiments may include filtering pulse oximeter measurements based on a gain applied to a current signal and a peak-to-peak voltage of a current signal. For example, one or more operations of method 300 described with reference to FIG. 3 and method 400 described with reference to FIG. 4 may be performed in conjunction to filter pulse oximeter measurements based on a gain applied to a current signal and a peak-to-peak voltage of a current signal.

Various embodiments may include indicating a quality of pulse oximeter measurements based on a gain applied to a received signal and a peak-to-peak voltage of a received signal. For example, one or more operations of method 300 described with reference to FIG. 3 and method 400 described with reference to FIG. 4 may be performed in conjunction to indicate a quality of pulse oximeter measurements based on a gain applied to a received signal and a peak-to-peak voltage of a received signal.

Figure 5:
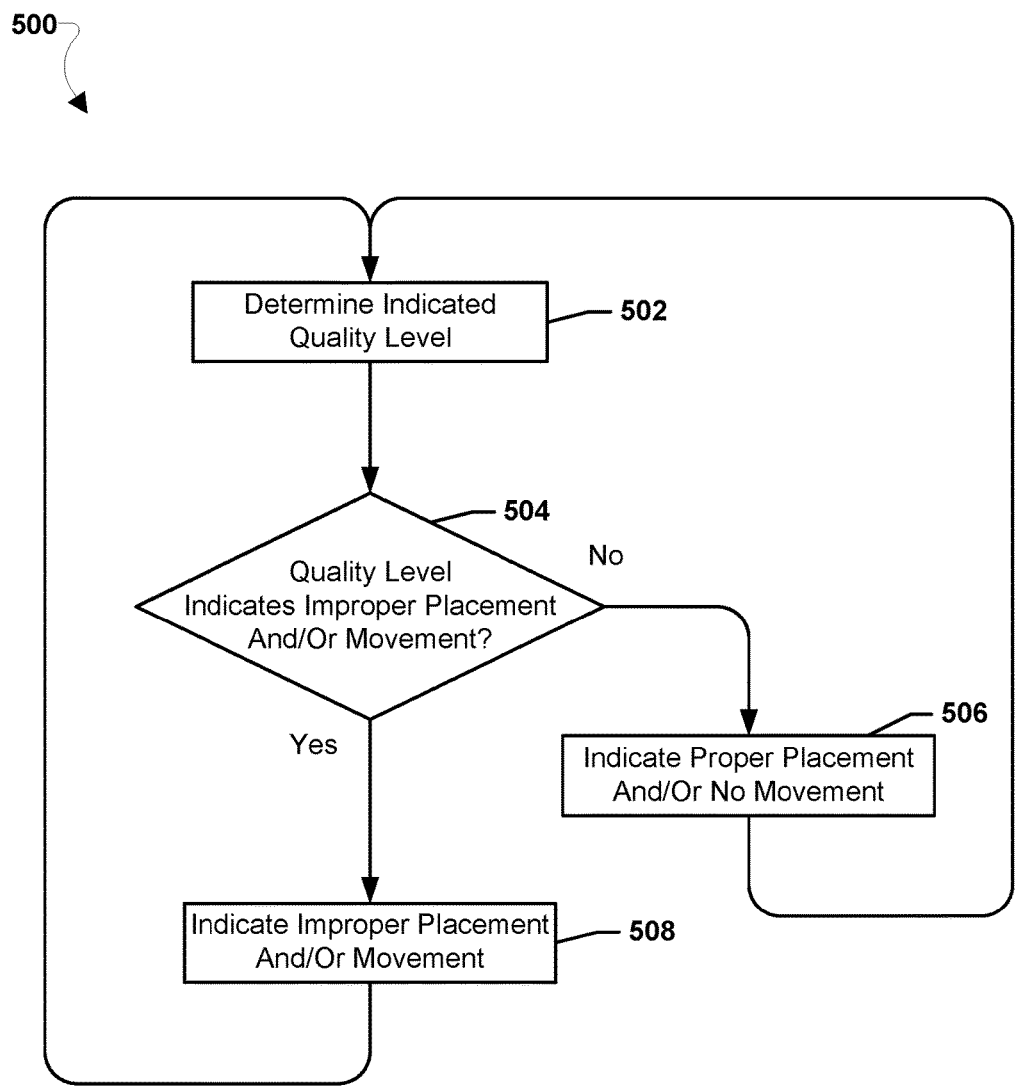
FIG. 5 is a process flow diagram illustrating a method for indicating improper placement and/or movement of a pulse oximeter based on a determined quality level of pulse oximeter measurements according to an embodiment.

FIG. 5 illustrates an embodiment method 500 for indicating improper placement and/or movement of a pulse oximeter based on a determined quality level of pulse oximeter measurements. In an embodiment, the operations of method 500 may be performed by a processor (e.g., processor 108) of an electronic patch including a pulse oximeter, such as patch 106. In various embodiments, the operations of method 500 may be performed by a processor in conjunction with the operations of the methods 300 and/or 400.

In block 502 the processor may determine an indicated quality level. As examples, the processor may determine the indicated quality level, based on the determined change in gain (e.g., continuous change in gain indicating the quality level is high, discontinuous change in gain indicating the quality level is low, etc.), based on the peak-to-peak voltage, by retrieving stored quality level indications from a memory, and/or by monitoring the transmissions of quality indications to a remote device, such as a smart phone.

In determination block 504, the processor may determine whether the quality level indicates an improper placement of the pulse oximeter and/or movement of patient. In some embodiments, indications of the quality of the blood oxygen level measurements and/or the pulse measurements may reflect the quality of the placement of the pulse oximeter and/or an amount of movement of the patient. For example, indications of low quality of the blood oxygen level measurements and/or the pulse measurements may be indications of improper placement of the pulse oximeter on a patient and/or an indication that the patient moved such that that the sensor elements lost contact with the patient's skin. In some embodiments, the processor of the pulse oximeter may determine the quality of the placement of the pulse oximeter and/or an amount of movement of the patient based on a determined a quality of the blood oxygen level measurements and/or the pulse measurements on a relative scale based on the gain applied and/or the peak-to-peak voltage. For example, by comparing the quality level indication to a minimum quality threshold associated with improper placement of the pulse oximeter on a patient and/or an indication that the patient moved such that that the sensor elements lost contact with the patient's skin, the processor may determine whether the quality level indicates an improper placement of the pulse oximeter and/or movement of patient. A quality indication below a certain level may indicate that the pulse oximeter is placed improperly and/or that the patient moved causing the sensor elements to lose contact with the patient's skin.

In response to determining that the quality level indicates proper placement and/or no patient movement (i.e., determination block 504="No"), the processor may indicate proper placement and/or no movement occurred in block 506. In some embodiments, processor may indicate proper placement and/or no movement occurred by transmitting indications of a quality of the placement of the pulse oximeter and/or an amount of movement of the patient to a remote device, such as a smart phone. For example, the processor of the pulse oximeter may send an indication that the pulse oximeter's placement is acceptable and/or no movement occurred (e.g., an "ok" message). As another example, the processor of the pulse oximeter may send a scale indication, such as a value between 1-10, reflecting the acceptability and/or lack of movement.

In response to determining that the quality level indicates an improper placement and/or unacceptable patient movement (i.e., determination block 504="Yes"), the processor may indicate improper placement and/or patient movement occurred in block 508. In some embodiments, processor may indicate proper placement and/or no movement occurred by transmitting indications of a quality of the placement of the pulse oximeter and/or an amount of movement of the patient to a remote device, such as a smart phone. For example, the processor of the pulse oximeter may send an indication that the pulse oximeter's placement is improper (e.g., a "move" message). As another example, the processor of the pulse oximeter may send an indication that the patient moved such that that the sensor elements lost contact with the patient's skin (e.g., a "warning" message). The indication that the pulse oximeter's placement is improper and/or the indication that the patient moved such that that the sensor elements lost contact with the patient's skin may be sent as scale indications, such as values between 1-10, reflecting the quality of the placement (e.g., high values being indicative of better placement than low values, or vice versa) and/or the amount of movement (e.g., high values being indicative of more movement than low values, or vice versa). In this manner, the scale may enable a user of the remote device, such as a smart phone, to determine an amount of movement needed to correctly position the pulse oximeter and/or a level of the degraded contact with the patient's skin.

Figure 6A:
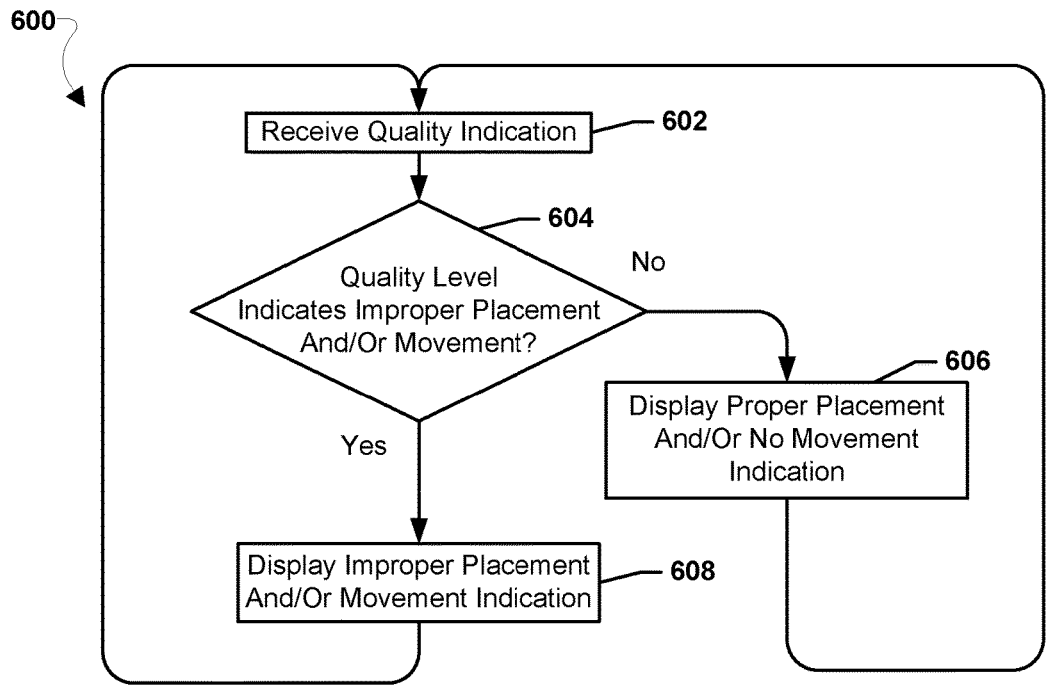
FIG. 6A is a process flow diagram illustrating a method for displaying an indication of improper placement and/or movement of a pulse oximeter based on a quality indication according to an embodiment.

FIG. 6A illustrates an embodiment method 600 for displaying an indication of improper placement and/or movement of a pulse oximeter based on a quality indication. In an embodiment, the operations of method 600 may be performed by a processor of computing device, such as a computing device in communication with an electronic patch including a pulse oximeter, such as patch 106. In various embodiments, the operations of method 600 may be performed by a processor in conjunction with the operations of methods 300, 400, and/or 600.

In block 602 the processor may receive a quality indication. As an example, the processor may receive the quality indication from a processor of an electronic patch including a pulse oximeter, such as patch 106. For example, the quality indication may be sent over a Bluetooth® link to the processor, such as a Bluetooth LE link. As examples, the quality indications may be the quality indications sent by the pulse oximeter according to the operations of methods 300, 400 and/or 500 described with reference to FIGS. 3, 4, and/or 5.

In determination block 604 the processor may determine whether the quality level indicates an improper placement of the pulse oximeter and/or movement of patient. In some embodiments, indications of the quality of the blood oxygen level measurements and/or the pulse measurements may be indications of a quality of the placement of the pulse oximeter and/or an amount of movement of the patient. For example, an indication of low quality of the blood oxygen level measurements and/or the pulse measurements may be an indication of improper placement of the pulse oximeter on a patient and/or an indication that the patient moved such that that the sensor elements lost contact with the patient's skin. In some embodiments, the processor may determine the quality of the placement of the pulse oximeter and/or an amount of movement of the patient based on a determined quality of the blood oxygen level measurements. For example, by comparing the quality level indication to a minimum quality threshold associated with improper placement of the pulse oximeter on a patient and/or an indication that the patient moved such that that the sensor elements lost contact with the patient's skin, the processor may determine whether the quality level indicates an improper placement of the pulse oximeter and/or movement of patient. A quality indication below a certain level may indicate that the pulse oximeter is placed improperly and/or the patient moved such that that the sensor elements lost contact with the patient's skin. In various embodiments, the quality indication may be a value indicative of the relative quality of the measurement on a scale, such as 1-10, that indicates the quality of the blood oxygen level measurements and/or the pulse measurements.

In response to determining that the quality level indicates proper placement and/or no patient movement (i.e., determination block 604="No"), the processor may display a proper placement and/or no movement indication in block 606. In some embodiments, the remote device may display an indication of proper placement of the pulse oximeter and/or an indication that the patient did not move as a message, a graphic, an audible command, or any other type indication perceptible to the user of the remote device such that the user of the remote device may be notified of the proper placement of the pulse oximeter and/or an indication that the patient has not moved.

In response to determining that the quality level indicates improper placement and/or patient movement (i.e., determination block 604="Yes"), the processor may display an improper placement and/or movement indication in block 608. In some embodiments, the remote device may display an indication of improper placement of the pulse oximeter and/or an indication that the patient moved as a message, a graphic, an audible command, or any other type indication perceptible to the user of the remote device such that the user of the remote device may be notified of the improper placement of the pulse oximeter and/or an indication that the patient moved. In this manner, the user of the remote device may be prompted to take an action regarding the placement of the pulse oximeter and/or the patient's movement, such as to adjust the placement of an electronic patch including the pulse oximeter on the patient.

Figure 6B:
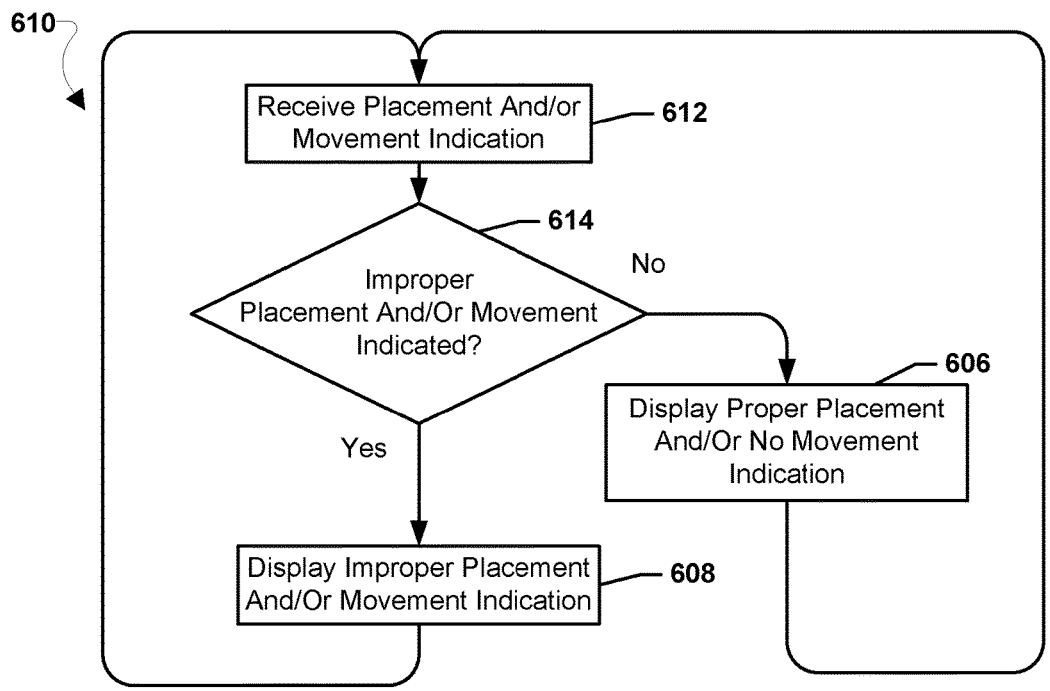
FIG. 6B is a process flow diagram illustrating a method for displaying an indication of improper placement and/or movement of a pulse oximeter based on placement and/or movement indication according to an embodiment.

FIG. 6B illustrates an embodiment method 610 for displaying an indication of improper placement and/or movement of a pulse oximeter based on placement and/or movement indication. In an embodiment, the operations of method 610 may be performed by a processor of computing device, such as a computing device in communication with an electronic patch including a pulse oximeter, such as patch 106. In various embodiments, the operations of method 610 may be performed by a processor in conjunction with the operations of methods 300, 400, 500, and/or 600.

In block 612 the processor may receive a placement and/or movement indication. As an example, the processor may receive the placement and/or movement indication from a processor of an electronic patch including a pulse oximeter, such as patch 106. For example, the placement and/or movement indication may be sent over a Bluetooth® link to the processor, such as a Bluetooth LE link. As an example, the placement and/or movement indication may be the placement and/or movement indication sent by the pulse oximeter according to the operations of blocks 506 and/or 508 of the method 500 described with reference to FIG. 5.

In determination block 614, the processor may determine whether improper placement or movement is indicated by the placement and/or movement indication. In various embodiments, improper placement and/or movement indications may be a value indicative of the relative improper placement and/or movement on a scale, such as 1-10, that indicates a level of improperness of the placement and/or a level of movement of the patient.

In response to the proper placement and/or no movement being indicated (i.e., determination block 614="No"), the processor may display a proper placement and/or no movement indication in block 606 as described with reference to FIG. 6A. In response to improper placement and/or movement being indicated (i.e., determination block 614="Yes"), the processor may display an improper placement and/or movement indication in block 608 as described with reference to FIG. 6A.

Figure 7:
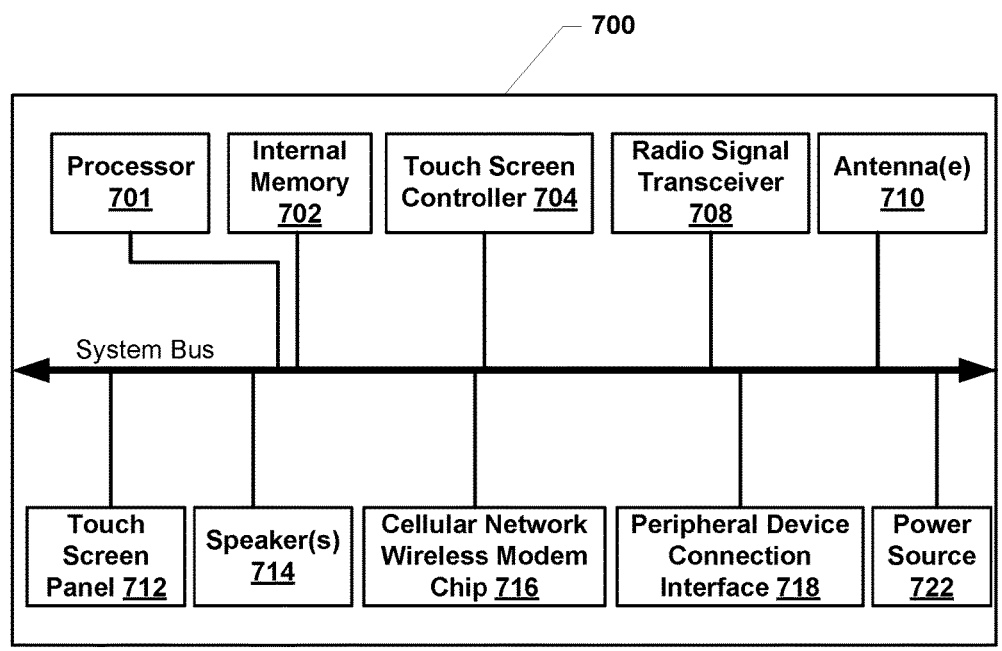
FIG. 7 is a component block diagram of a computing device suitable for use with various embodiments.

An embodiment patch may be configured to transmit data to any of a variety of computing devices. For example, FIG. 7 illustrates a computing device 700 suitable for use in various embodiments. The computing device 700 may exchange data from the electronic patches discussed above, and may perform one or more of the operations of methods 300, 400, 500, 600, and/or 610 described with reference to FIGS. 3, 4, 5, 6A, and/or 6B. As examples, pulse oximeter measurements, quality indications, placement indications, and/or movement indications may be sent to the computing device 700 from a processor of an electronic patch including a pulse oximeter, such as patch 106. As another example, pulse oximeter control signals may be sent to a processor of an electronic patch including a pulse oximeter and accelerometer, such as patch 106, from the computing device 700.

In various embodiments, the computing device 700 may include a processor 701 coupled to a touch screen controller 704 and an internal memory 702. The processor 701 may be one or more multicore ICs designated for general or specific processing tasks. The internal memory 702 may be volatile or non-volatile memory, and may also be secure and/or encrypted memory, or unsecure and/or unencrypted memory, or any combination thereof. The touch screen controller 704 and the processor 701 may also be coupled to a touch screen panel 712, such as a resistive-sensing touch screen, capacitive-sensing touch screen, infrared sensing touch screen, etc.

The computing device 700 may have one or more radio signal transceivers 708 (e.g., Peanut®, Bluetooth®, Zigbee®, WLAN, RF, cellular, etc.) and antennae 710, for sending and receiving, coupled to each other and/or to the processor 701. The transceivers 708 and antennae 710 may be used with the above-mentioned circuitry to implement the various wireless transmission protocol stacks and interfaces. The computing device 700 may include a cellular network wireless modem chip 716 that enables communication via a cellular network, such as an eMBMS network, and is coupled to the processor.

The computing device 700 may include a peripheral device connection interface 718 coupled to the processor 701. The peripheral device connection interface 718 may be singularly configured to accept one type of connection, or configured to accept various types of physical and communication connections, common or proprietary, such as USB, FireWire, Thunderbolt, or PCIe. The peripheral device connection interface 718 may also be coupled to a similarly configured peripheral device connection port (not shown).

The computing device 700 may also include a housing, constructed of a plastic, metal, or a combination of materials, for containing all or some of the components discussed herein. The computing device 700 may include a power source 722 coupled to the processor 701, such as a disposable or rechargeable battery. The rechargeable battery may also be coupled to the peripheral device connection port to receive a charging current from a source external to the computing device 700. The computing device 700 may also include speakers 714 for providing audio outputs.

Various embodiments may include a device including means for obtaining a gain of a first signal generated by the one or more sensors, wherein the one or more sensors are positioned on a subject's body, means for determining a gain of a second signal generated by the one or more sensors, and means for generating a contact quality based on a comparison of the first signal's gain and the second signal's gain, wherein the contact quality corresponds to a level of contact between the one or more sensors and the subject's body. In some embodiments, means for generating a contact quality based on the comparison of the first signal's gain and the second signal's gain may include means for comparing the first signal's gain, the second signal's gain, and one or more thresholds. Some embodiments may include means for adjusting one or more sensing modalities of the one or more sensors based on the contact quality. In some embodiments, a low contact quality may indicate improper placement of the one or more sensors, movement of the subject, or any combination thereof. Some embodiments may include means for filtering one or more measurements from the one or more sensors based on a comparison of the contact quality and at least one of a second threshold, wherein the one or more measurements are associated with the second signal. In some embodiments, the means for obtaining, means for determining, and means for generating may operate after changes in gain applied have stabilized to account for the subject's body skin type and color.

Various embodiments may include a device including means for determining a peak-to-peak voltage of a received signal from the one or more sensors, and means for generating a contact quality based on the peak-to-peak voltage and one or more thresholds, wherein the contact quality corresponds to a level of contact between the one or more sensors and the subject's body. Some embodiments may include means for filtering one or more measurements from the one or more sensors associated with the received signal based on a comparison of the contact quality and one or more thresholds. In some embodiments, the contact quality may indicate improper placement of the one or more sensors, movement of the subject, or any combination thereof.

Various embodiments may include non-transitory media having stored thereon processor executable instructions configured to cause a processor of a device to perform operations including obtaining a gain of a first signal generated by the one or more sensors, wherein the one or more sensors are positioned on a subject's body, determining a gain of a second signal generated by the one or more sensors, and generating a contact quality based on a comparison of the first signal's gain and the second signal's gain, wherein the contact quality corresponds to a level of contact between the one or more sensors and the subject's body. In some embodiments, the stored processor executable instructions may be configured to cause a processor of a device to perform operations such that generating a contact quality based on the comparison of the first signal's gain and the second signal's gain may include comparing the first signal's gain, the second signal's gain, and one or more thresholds. Some embodiments may include the stored processor executable instructions being configured to cause a processor of a device to perform operations including adjusting one or more sensing modalities of the one or more sensors based on the contact quality. In some embodiments, the stored processor executable instructions may be configured to cause a processor of a device to perform operations such that a low contact quality may indicate improper placement of the one or more sensors, movement of the subject, or any combination thereof. In some embodiments, the stored processor executable instructions may be configured to cause a processor of a device to perform operations including filtering one or more measurements from the one or more sensors based on a comparison of the contact quality and at least one of a second threshold, wherein the one or more measurements are associated with the second signal. In some embodiments, the stored processor executable instructions may be configured to cause a processor of a device to perform operations such that the obtaining, determining, and generating may be performed after changes in gain applied have stabilized to account for the subject's body skin type and color.

Various embodiments may include non-transitory media having stored thereon processor executable instructions configured to cause a processor of a device to perform operations including determining a peak-to-peak voltage of a received signal from the one or more sensors, and generating a contact quality based on the peak-to-peak voltage and one or more thresholds, wherein the contact quality corresponds to a level of contact between the one or more sensors and the subject's body. In some embodiments, the stored processor executable instructions may be configured to cause a processor of a device to perform operations including filtering one or more measurements from the one or more sensors associated with the received signal based on a comparison of the contact quality and one or more thresholds. In some embodiments, the stored processor executable instructions may be configured to cause a processor of a device to perform operations such that the contact quality may indicate improper placement of the one or more sensors, movement of the subject, or any combination thereof.

Further, those of skill in the art will appreciate that the foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope embodiments.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The functions in the various embodiments may be implemented in hardware, software, firmware, or any combination thereof. If implemented in software, the functions may be stored as one or more processor executable instructions or code on a non-transitory computer readable medium or non-transitory processor readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method for determining measurement quality of one or more measurements from one or more sensors, comprising:

obtaining, at a processor, a first amplification gain for a first signal generated by the one or more sensors, wherein the one or more sensors are positioned on a subject's body, and wherein the first amplification gain is for amplifying or reducing the first signal to within a first pre-determined level at a first time;

determining, at the processor, a second amplification gain for a second signal generated by the one or more sensors, wherein the second amplification gain is for amplifying or reducing the second signal to within a second pre-determined level at a second time after the first time; and generating, at the processor, a contact quality value of a contact between the one or more sensors and the subject's body based on a degree of change between the first amplification gain and the second amplification gain with respect to time.

2. The method of claim 1, wherein the generating the contact quality value based on the degree of change between the first amplification gain and the second amplification gain further comprises comparing the first amplification gain, the second amplification gain, and one or more thresholds.

3. The method of claim 1, further comprising:
adjusting one or more sensing modalities of the one or more sensors based on the contact quality value.

4. The method of claim 1, wherein a contact quality value less than a predetermined threshold indicates improper placement of the one or more sensors, movement of the subject, or any combination thereof.

5. The method of claim 1, further comprising:
filtering one or more measurements from the one or more sensors based on a comparison of the contact quality value and at least one threshold of a set of thresholds, wherein the one or more measurements are associated with the second signal.

6. The method of claim 1, wherein obtaining the first amplification gain, determining the second amplification gain, and generating the contact quality value based on the degree of change between the first amplification gain and the second amplification gain are performed after changes in a third amplification gain applied to at least one of the first signal or the second signal within a third time before the first time have stabilized to account for the subject's body skin type and color.

7. The method of claim 1, wherein generating the contact quality value of the contact between the one or more sensors and the subject's body based on the degree of change between the first amplification gain and the second amplification gain with respect to time comprises generating the contact quality value based on a gain difference between the first amplification gain and the second amplification gain.

8. The method of claim 7, wherein generating the contact quality value of the contact between the one or more sensors and the subject's body based on the degree of change between the first amplification gain and the second amplification gain with respect to time comprises generating the contact quality value based on whether the gain difference exceeds a difference threshold.

9. The method of claim 7, wherein generating the contact quality value of the contact between the one or more sensors and the subject's body based on the degree of change between the first amplification gain and the second amplification gain with respect to time comprises generating the contact quality value based on a gain change rate based on a ratio between the gain difference and a time elapsed between the first time and the second time.

10. The method of claim 9, wherein generating the contact quality value of the contact between the one or more sensors and the subject's body based on the degree of change between the first amplification gain and the second amplification gain with respect to time comprises generating the contact quality value based on whether the gain change rate exceeds a rate threshold.

11. The method of claim 1, further comprising:
obtaining, at the processor, a third amplification gain for the signal, wherein the third amplification gain is associated with a third time prior to the second time; and determining, by the processor, an average amplification gain based on an average between the first amplification gain and the third amplification gain;

wherein the contact quality value is generated based on a gain difference between the average amplification gain and the second amplification gain.

12. The method of claim 1, wherein generating the contact quality value of the contact between the one or more sensors and the subject's body based on the degree of change between the first amplification gain and the second amplification gain with respect to time comprises maintaining the contact quality value based on the degree of change falling with a pre-determined range.

13. A device, comprising:
one or more sensors; and
a processor coupled to the one or more sensors, wherein the processor is configured to:
obtain a first amplification gain for a first signal generated by the one or more sensors, wherein the one or more sensors are positioned on a subject's body, the first amplification gain being for amplifying the first signal to within a first pre-determined level at a first time;
determine a second amplification gain for a second signal generated by the one or more sensors, the second amplification gain being for amplifying the first signal to within a first pre-determined level at a second time after the first time; and
generate a contact quality value of a contact between the one or more sensors and the subject's body based on a degree of change between of the first amplification gain and the second amplification gain with respect to time.

14. The device of claim 13, wherein the processor is configured such that generating a contact quality value based on the degree of change between the first amplification gain and the second amplification gain further comprises comparing the first amplification gain, the second amplification gain, and one or more thresholds.

15. The device of claim 13, wherein the processor is further configured to adjust one or more sensing modalities of the one or more sensors based on the contact quality value.

16. The device of claim 13, wherein a contact quality value less than a predetermined threshold indicates improper placement of the one or more sensors, movement of the subject, or any combination thereof.

17. The device of claim 13, wherein the processor is further configured to filter one or more measurements from the one or more sensors based on a comparison of the contact quality value and at least one threshold of a set of thresholds, wherein the one or more measurements are associated with the second signal.

18. The device of claim 13, wherein the processor is configured such that obtaining the first amplification gain, determining the second amplification gain, and generating the contact quality value based on the degree of change between the first amplification gain and the second amplification gain are performed after changes in a third amplification gain applied to at least one of the first signal or the second signal within a third time before the first time have stabilized to account for the subject's body skin type and color.

19. The device of claim 13, wherein:
the first amplification gain is a gain applied to amplify or reduce an amplitude of the first signal at the first time; and
the second amplification gain is a gain applied to amplify or reduce an amplitude of the second signal at the second time.

20. The device of claim 13, wherein the processor is configured such that generating the contact quality value of the contact between the one or more sensors and the subject's body based on the degree of change between the first amplification gain and the second amplification gain with respect to time comprises maintaining the contact quality value based on the degree of change falling with a pre-determined range.

21. A device, comprising:
one or more sensors configured to be coupled to a subject's body and, when coupled to the subject's body, output a signal indicative of a physiological property of the subject, wherein the one or more sensors include:
a generator configured to generate a respective stimulus to the subject's body; and
a transducer configured to receive the stimulus subsequent to the stimulus being modified by the subject's body and output a signal indicative of the modified stimulus; and
a processor coupled to the one or more sensors, wherein the processor is configured to:
obtain a first amplification gain value indicative of an amplification gain applied, at first time, to one of a first signal transmitted to the generator corresponding to generating of the stimulus or a second signal received from the transducer corresponding to the transducer receiving the modified stimulus, the first amplification gain being for amplifying or reducing the first signal or the second signal to within a first pre-determined level at the first time;
determine a second amplification gain value of an amplification gain applied, at a second time after the first time, to one of the first signal or the second signal, the second amplification gain being for amplifying or reducing the first signal or the second signal to within a second pre-determined level at the second time; and
generate a contact quality value of a contact between the one or more sensors and the subject's body based on a degree of change between the first amplification gain value and the second amplification gain value with respect to time.

22. The device of claim 21, wherein the processor is configured such that generating the contact quality value of the contact between the one or more sensors and the subject's body based on the degree of change between the first amplification gain and the second amplification gain with respect to time comprises maintaining the contact quality value based on the degree of change falling with a pre-determined range.

23. The device of claim 21, wherein the level of contact is indicative of:
a proximity of at least one of the one or more sensors to at least a portion of the subject's body;
an amount of movement of the subject; or
an accuracy of a placement of at least one of the one or more sensors on the subject's body.

24. The device of claim 21, further comprising an automatic amplification gain control loop circuit, and wherein the signal transmitted to the generator corresponding to generating of the stimulus and the signal received from the transducer corresponding to the transducer receiving the modified stimulus of the first amplification gain value and the second amplification gain value are:
applied by the automatic amplification gain control loop circuit.

25. The device of claim 24, wherein the automatic amplification gain control loop circuit is configured to amplify or reduce the stimulus generated by the generator to mitigate a corresponding signal from exceeding a range, the corresponding signal generated by the transducer in response to receiving the stimulus.

* * * * *